(12) United States Patent
Wang

(10) Patent No.: US 10,702,410 B2
(45) Date of Patent: Jul. 7, 2020

(54) JOINT ANGLE ADJUSTMENT MECHANISM

(71) Applicant: Meng-Chun Wang, Taichung (TW)

(72) Inventor: Meng-Chun Wang, Taichung (TW)

( * ) Notice: Subject to any disclaimer, the term of this patent is extended or adjusted under 35 U.S.C. 154(b) by 581 days.

(21) Appl. No.: 15/488,068

(22) Filed: Apr. 14, 2017

(65) Prior Publication Data

US 2018/0296380 A1     Oct. 18, 2018

(51) Int. Cl.
   *A61F 5/01*     (2006.01)

(52) U.S. Cl.
   CPC .......... *A61F 5/0102* (2013.01); *A61F 5/0125* (2013.01); *A61F 2005/0158* (2013.01); *A61F 2005/0167* (2013.01); *A61F 2005/0179* (2013.01)

(58) Field of Classification Search
   CPC ...... A61F 2005/0167; A61F 2005/0158; A61F 2005/0137; A61F 5/01; A61F 5/0102; A61F 5/0125; A61F 5/0123
   USPC ..... 602/5, 6, 16, 23, 26; 601/33, 34, 35, 29; 128/845, 882, 892
   See application file for complete search history.

(56) References Cited

U.S. PATENT DOCUMENTS

| 2006/0247565 A1* | 11/2006 | Cormier ................ A61F 5/0125 602/16 |
| 2015/0018735 A1* | 1/2015 | Chetlapalli ........... A61F 5/0123 602/16 |
| 2017/0156910 A1* | 6/2017 | Wang .................... A61F 5/0102 |

FOREIGN PATENT DOCUMENTS

TW          M336776 U        7/2008

* cited by examiner

*Primary Examiner* — Anna K Kinsaul
*Assistant Examiner* — Caitlin A Carreiro
(74) *Attorney, Agent, or Firm* — Muncy, Geissler, Olds & Lowe, P.C.

(57) ABSTRACT

A joint angle adjustment mechanism is provided. A base has a center and two side boards opposite to each other, and at least one of the two side boards has toothed recesses arranged curvedly and open toward the center. Two connecting members are respectively connected to the base, and at least one of the two connecting members is pivoted to the base. At least one adjustment mechanism is axially pivoted to the base about the center, each said adjustment mechanism includes a positioning assembly including a slidable seat, a positioning member and an elastic member within the slidable seat, the positioning member is slidably arranged within the slidable seat and optionally moves radially to be engaged with or disengaged from one of the toothed recesses, the elastic member radially urges the positioning member to engage with one of the toothed recesses.

9 Claims, 9 Drawing Sheets

US 10,702,410 B2

JOINT ANGLE ADJUSTMENT MECHANISM

BACKGROUND OF THE INVENTION

Field of the Invention

The present invention relates to a joint angle adjustment mechanism.

Description of the Prior Art

Usually, when a person's limb(s) is injured, especially joint(s) (for example, knee(s)), an assistive device is often used, during a healing or recovery process, to restrict the movement of the limb(s) so as to prevent the injured part(s) from getting hurt again or worsen due to over-exercising. However, it is understandable that this type of assistive device can also be used to correct body posture, and this type of angle adjustable joint fixer is disclosed in TWM336776.

However, the conventional angle adjustable joint fixer is positioned through a positioning pin inserted into a positioning hole. However, when the angle adjustable joint fixer is used on the elderly or children who are physically weaker, the positioning pin are often unable to be inserted into or pulled out of the positioning hole since the elderly or children are unable to move fast and manipulate precisely. Therefore, the joint fixer cannot be positioned firmly and thus cannot protect the injured part thoroughly.

The present invention has arisen to mitigate and/or obviate the afore-described disadvantages.

SUMMARY OF THE INVENTION

The major object of the present invention is to provide a joint angle adjustment device, which provides an angle adjustable joint fixer to easily move an adjustment mechanism to adjust an angle a user wants. The joint angle adjustment device has a simple structure and can be positioned stably so as to enhance user safety.

To achieve the above and other objects, a joint angle adjustment mechanism is provided, including a base, two connecting members and a positioning mechanism. The base has a center and two side boards opposite to each other, the center defines an axial direction, at least one of the two side boards has a plurality of toothed recesses relative to the center, the plurality of toothed recesses are arranged curvedly, and an opening of each said toothed recess faces the center. The two connecting members are respectively connected to the base, and at least one of the two connecting members is pivoted to the base. The positioning mechanism includes at least one adjustment mechanism, each said adjustment mechanism is axially pivoted to the base about the center, each said adjustment mechanism includes a positioning assembly, the positioning assembly includes a slidable seat, a positioning member and an elastic member, the positioning member is slidably arranged within the slidable seat and optionally moves radially to be engaged with or disengaged from one of the toothed recesses, the elastic member is arranged within the slidable seat, two ends of the elastic member curl and bend relatively inward, the elastic member abuts against the positioning member so that the positioning member has a tendency to be radially engaged with one of the toothed recesses.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

Figure 1:
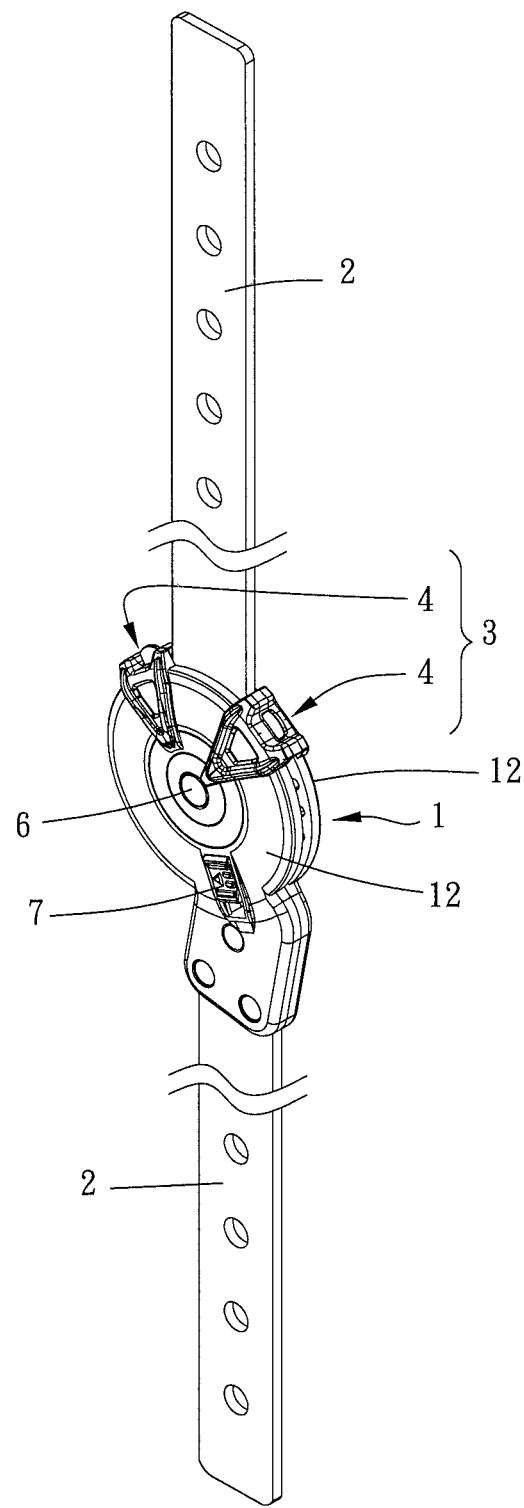
FIG. 1 is a stereogram of a preferred embodiment of the present invention.
Figure 2:
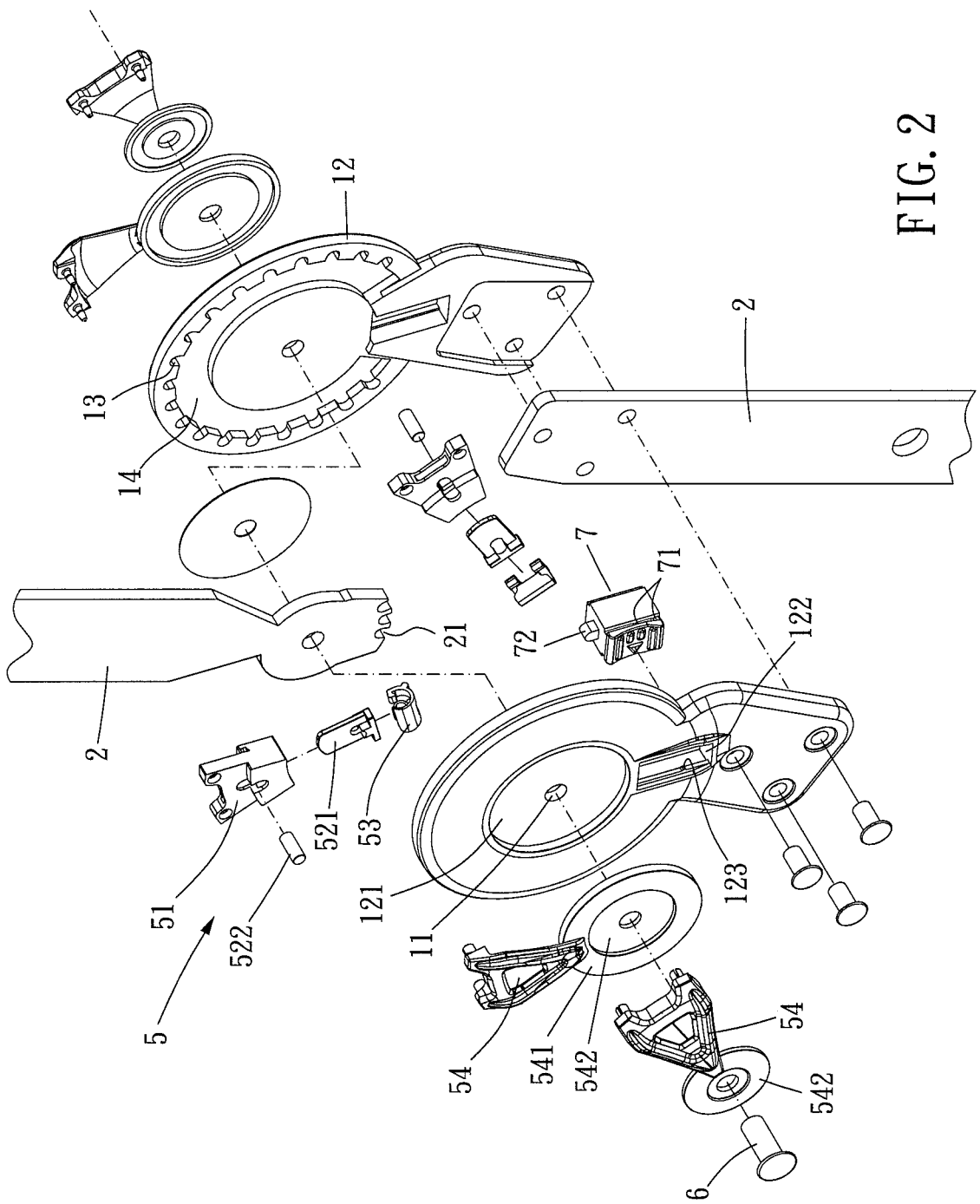
FIG. 2 is a breakdown view of the preferred embodiment of the present invention.
Figure 3:
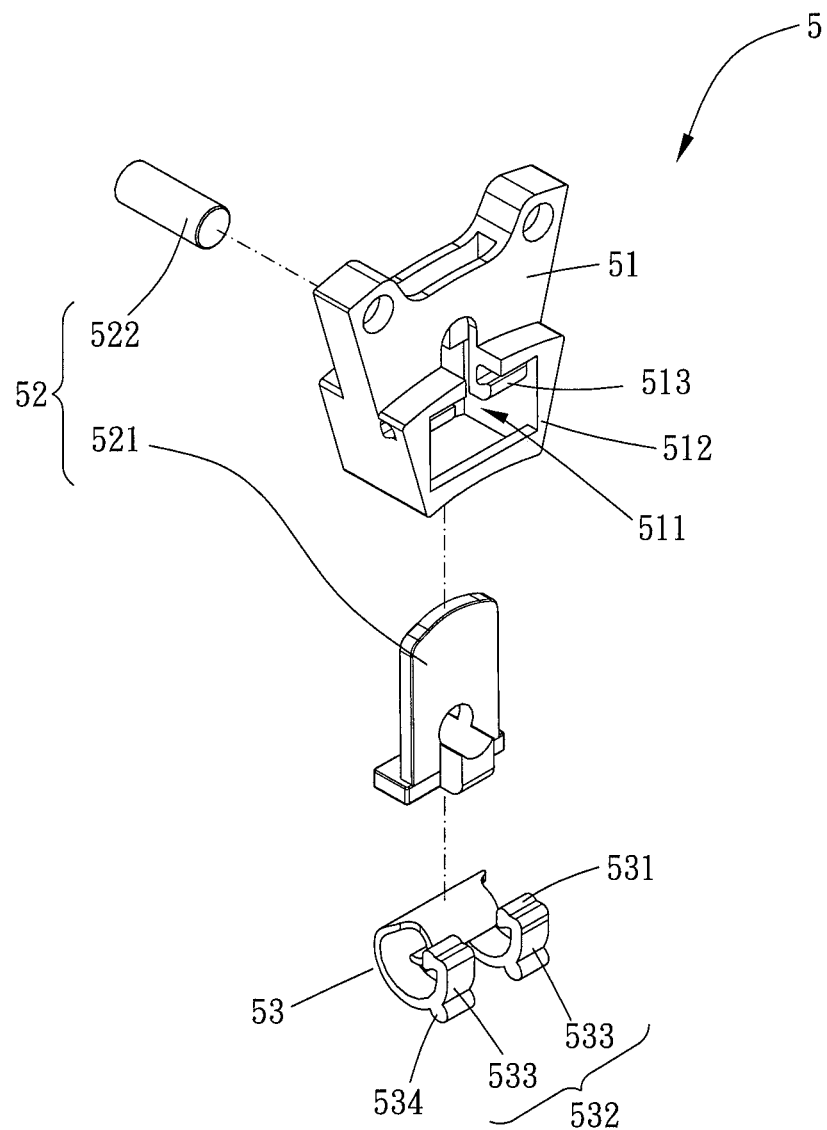
FIG. 3 is a partially breakdown view of the preferred embodiment of the present invention.

The present invention will be clearer from the following description when viewed together with the accompanying drawings, which show, for purpose of illustrations only, the preferred embodiment in accordance with the present invention.

Please refer to FIGS. 1 to 9 for a preferred embodiment of the present invention, a joint angle adjustment mechanism includes a base 1, two connecting members 2 and a positioning mechanism 3.

The base 1 has a center 11 and two side boards 12 opposite to each other, the center 11 defines an axial direction, at least one of the two side boards 12 has a plurality of toothed recesses 13 relative to the center, the plurality of toothed recesses 13 are arranged curvedly, an opening of each said toothed recess 13 faces the center 11, and in this embodiment, both the two side boards 12 have the plurality of toothed recesses 13.

Figure 10:
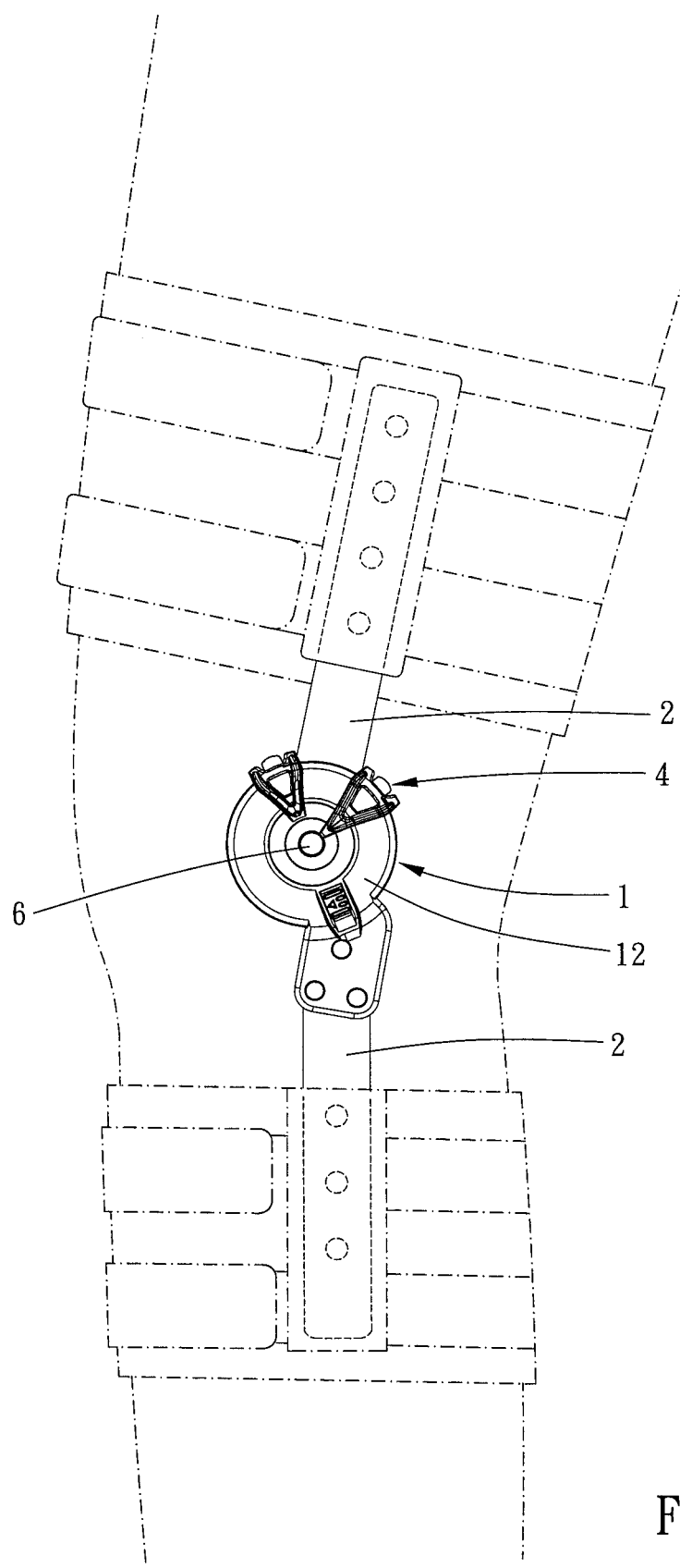
FIG. 10 is a drawing showing the preferred embodiment of the present invention in use.

The two connecting members 2 are respectively connected to the base 1, and at least one of the two connecting members 2 is pivoted to the base 1. In this embodiment, only one of the two connecting members 2 is pivoted to the base 1, and the two connecting members 2 are respectively provided for being fixed on parts of a limb on the two sides of a joint (as shown in FIG. 10).

The positioning mechanism 3 includes at least one adjustment mechanism 4, each said adjustment mechanism 4 is axially pivoted to the base 1 about the center 11, in this embodiment, the positioning mechanism 4 includes two said adjustment mechanisms 4, each said adjustment mechanism 4 includes a positioning assembly 5, the positioning assembly 5 includes a slidable seat 51, a positioning member 52 and an elastic member 53, the positioning member 52 is slidably arranged within the slidable seat 51 and optionally moves radially to be engaged with or disengaged from one of the toothed recesses 13, the elastic member 53 is arranged within the slidable seat 51, two ends of the elastic member 53 curl and bend relatively inward, the elastic member 53 abuts against the positioning member 52 so that the positioning member 52 has a tendency to be radially engaged with one of the toothed recesses 13; therefore, the two adjustment mechanisms 4 normally cannot swing relative to the base 1 randomly, when the connecting member 2 which is pivoted to the base 1 swings, a swinging angle of the connecting member 2 is restricted by the two adjustment mechanisms 4, when the positioning member 5 is operated by a force to be disengaged from one of the toothed recesses 13, the adjustment mechanism 4 can swing relative to the base 1 to adjust a restriction angle of the two connecting members 2 swinging relative to each other, and when the adjustment mechanism 4 swings to the angle to be adjusted and the positioning member 5 is not driven by the force, the positioning member 52 can be engaged with one of the toothed recesses 13 to enhance user safety.

Each said slidable seat 51 has a receiving space 511 therein, a side of each said slidable seat 51 along the axial direction has an opening 512 which communicates with the receiving space 511, each said positioning member 52 includes a slidable block 521 and a pin member 522, the slidable block 521 is slidably arranged within the receiving space 511, the pin member 522 is inserted between the slidable seat 51 and the slidable block 521, and the pin member 522 is normally engaged with one of the toothed recesses 13.

The slidable seat 51 has at least one first hook portion 513 in the receiving space 511, one of the two ends of the elastic member 53 forms at least one second hook portion 531, in this embodiment, there are two said first hook portions 513 and two said second hook portions 531, the at least one first hook portion 513 and the at least one second hook portion 531 hook with each other, the two first hook portions 513 are respectively hook with the two second hook portions 531, and the other of the two ends of the elastic member 53 opposite to the two second hook portions 531 abuts against the slidable block 521.

Figure 4:
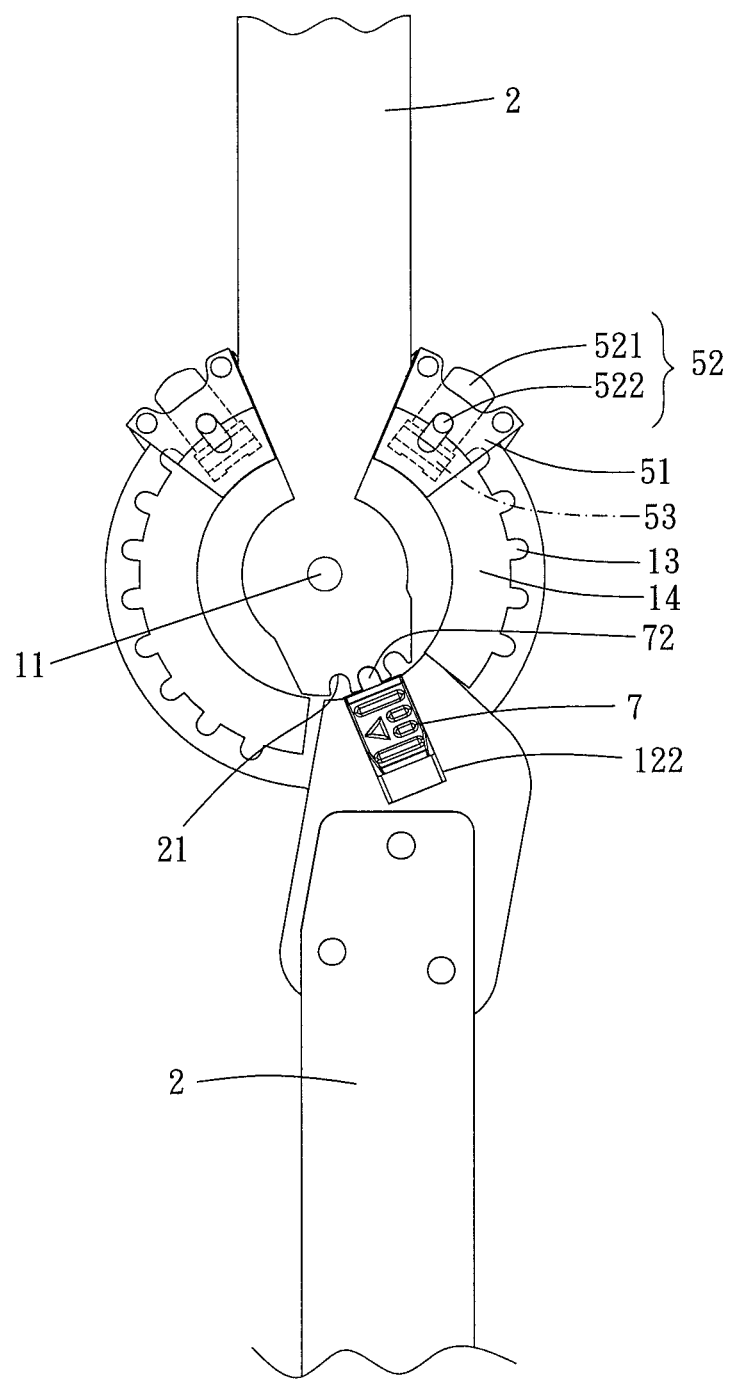
FIGS. 4 to 7 are side views showing the preferred embodiment of the present invention in operation.

Specifically, one of the two ends of the elastic member 53 forms a forked section 532 which has two leg portions 533, the two leg portions 533 curl and bend and have one of the second hook portions 531, a side of the two leg portions 533 toward outside further has a supporting portion 534 protruding therefrom, and the two supporting portions 534 abut against a stepped portion 514 in the receiving space 511; therefore, with the two second hook portions 531 hooking with the two first hook portions 513 and the supporting portion 534 abutting against the stepped portion 514, the elastic member 53 can be stably fixed on the slidable seat 51 so as to abut the slidable block 521 normally toward a direction away from the center 11 (as shown in FIG. 4).

Figures 5, 6:
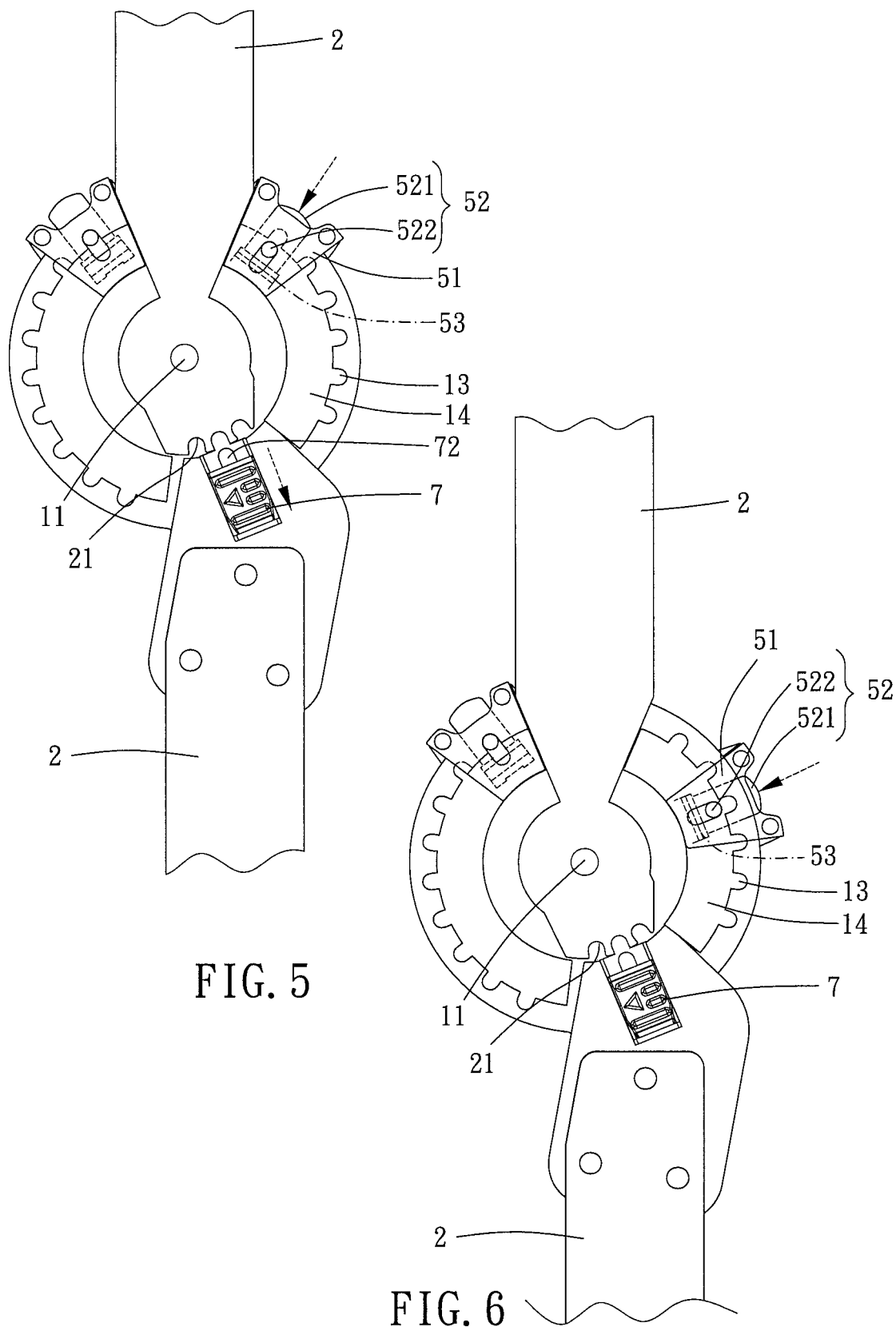

Each said adjustment mechanism 4 further has a movable seat 54 which is pivoted to the base 1, each said movable seat 54 is saddled on the base 1, each said positioning assembly 5 is arranged in one of the movable seats 54, one of two ends of the slidable block 521 is disposed through and protrudes beyond the movable seat 54 and the slidable seat 51, in this embodiment, faces of the two side boards 12 facing each other further respectively have a curved annular groove 14, the curved annular groove 14 communicates with the toothed recesses 13, each said slidable seat 51 is slidably arranged between the two curved annular grooves 14, the slidable block 521 is operable from outside to drive the pin member 522 to move radially to be engaged with or disengaged from one of the toothed recesses 13, and when the pin member 522 is disengaged from one of the toothed recesses 13 (as shown in FIG. 5), by swinging the movable seat 54, then the slidable seat 51 and the positioning assembly 5 can be driven to move in the base 1 (as shown in FIG. 6) to adjust the restriction angle.

Each of faces of the two side boards 12 opposite to each other has a first pivotal groove 121, each said movable seat 54 has two arm portions 541, each of the two arm portions 541 of one of the two movable seats 54 is pivoted to one said first pivotal groove 121, each of the two arm portions 541 of the movable seat 54 which is pivoted to one said pivotal first grooves 121 further has a second pivotal groove 542, each of the two arm portions 541 of the other of the two movable seats 54 is pivoted to one said second pivotal grooves 542, and a pivot shaft 6 is disposed through the two side boards 12 and the two arm portions 541 of the two movable seats 54 so as to make the two movable seats 54 to swing relative to the base 1 without interfering with the base 1.

Figure 7:
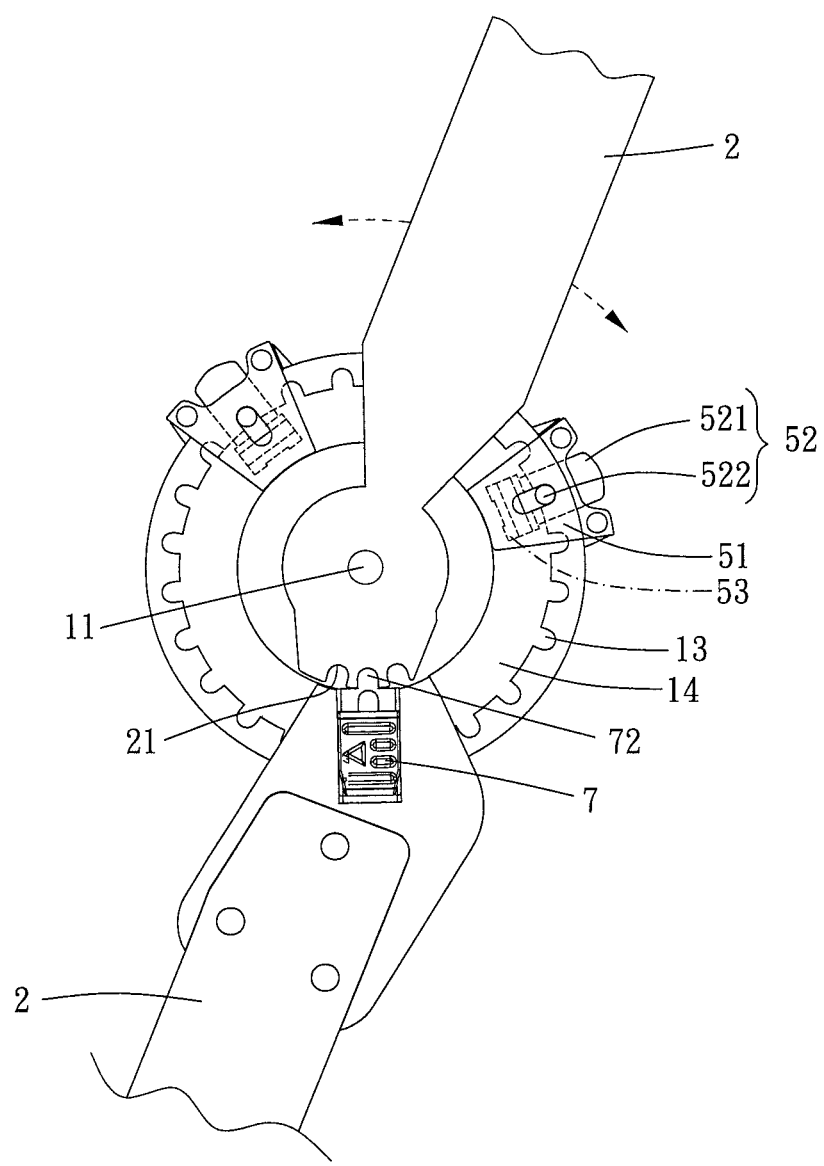
Figure 8:
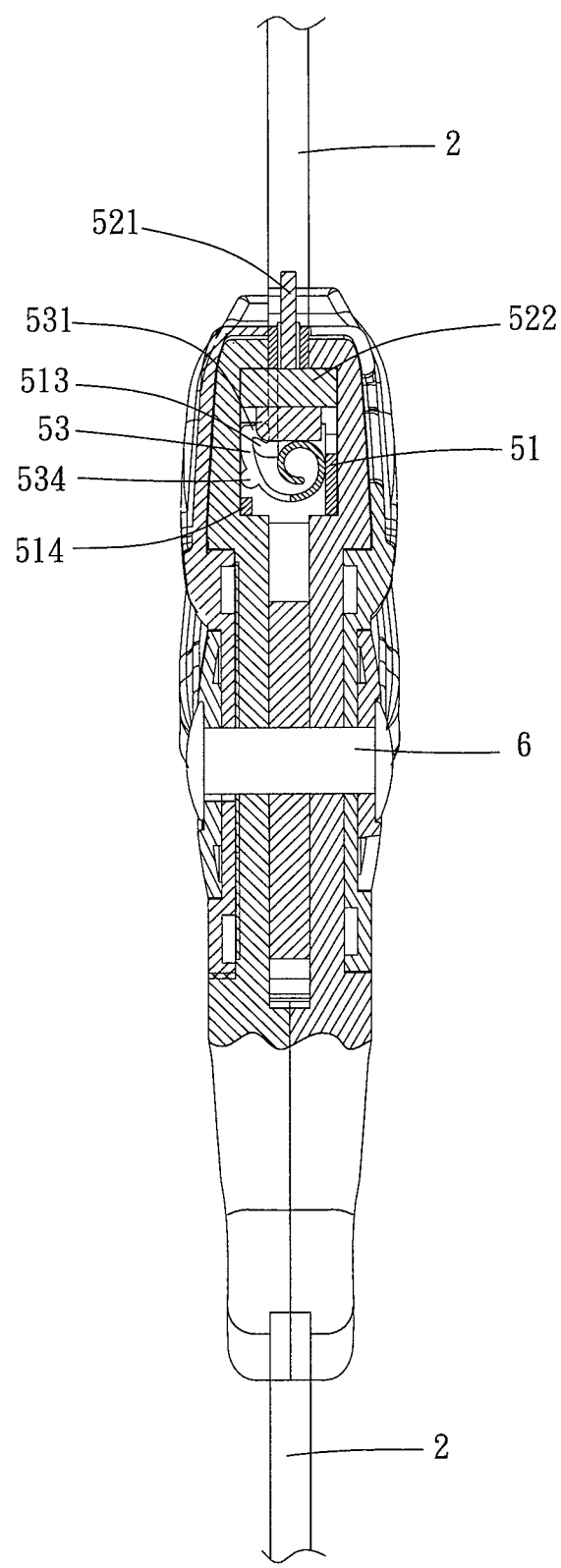
FIGS. 8 and 9 are cross-sectional views showing the preferred embodiment of the present invention in operation.
Figure 9:
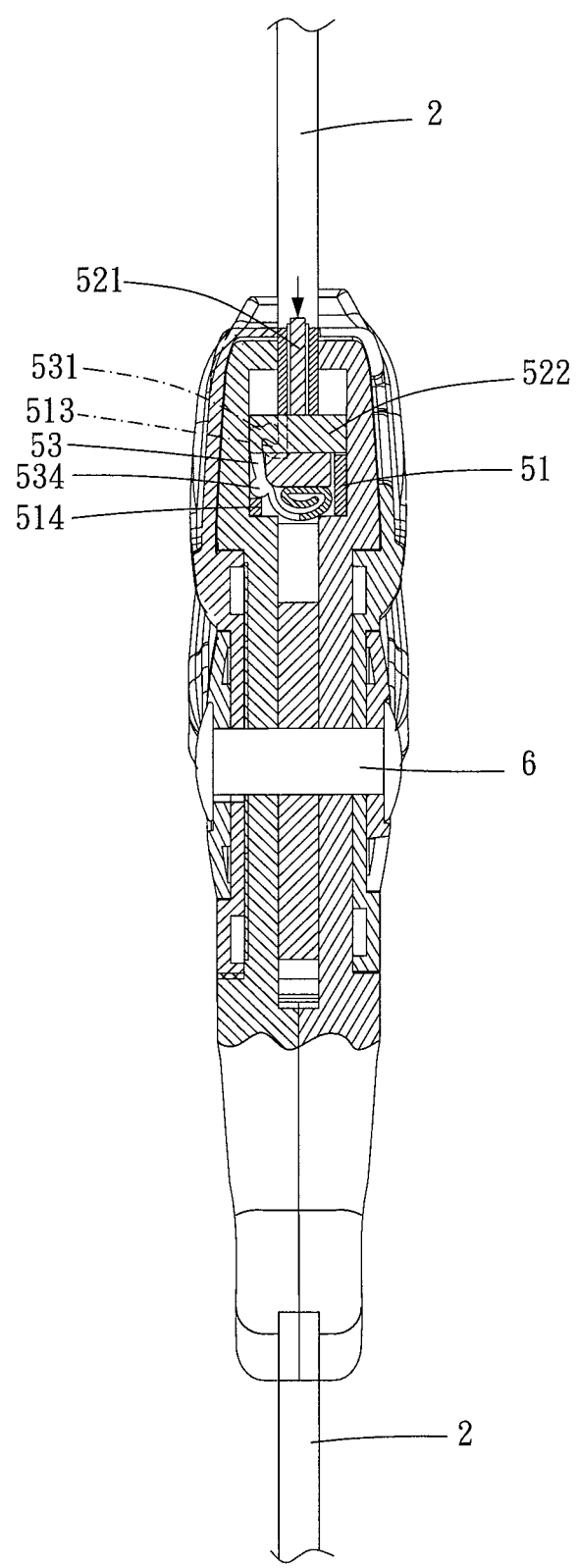

One of the two connecting members 2 is fixed on the base 1, the other of the two connecting members 2 is pivoted to the base 1, the joint angle adjustment mechanism further includes a lock member 7, the lock member 7 is arranged on the base 1 and movable to be in a first position and a second position, when the lock member 7 is in the first position, the lock member 7 unrestricts the connecting member 2 which is pivoted to the base 1 (as shown in FIGS. 5 to 7), and when the lock member 7 is in the second position, the lock member 7 restricts the connecting member 2 which is pivoted to the base 1 so that the connecting member 2 is unswingable relative to the base 1 (as shown in FIG. 4); that is, an angle between the two connecting members 2 is completely locked. Preferably, the connecting member 2 which is pivoted to the base 1 has a plurality of tooth portions 21 radially thereon, the lock member 7 has a restricting protrusion 72 radially thereon, when the lock member 7 is in the first position, the restricting protrusion 72 restricts one of the tooth portions 21, and the user can choose to make the restriction protrusion 72 to restrict one of the tooth portion 21 to adjust the angle of the two connecting members 2 when locked.

Each of the faces of the two side boards 12 facing each other has a sliding slot 122 radially therein, the lock member 7 is slidably arranged in the sliding slot 122, the sliding slot 122 has a first fastening portion 123, the lock member 7 has two second fastening portions 71, and when the lock member 7 is in the first and second positions, the first fastening portion 123 is correspondingly engaged with one of the two second fastening portions 71 to prevent the lock member 7 from sliding randomly. If the user wants to move the lock member 7, s/he only needs to apply a force on the first fastening portion 123 to make the first fastening portion 123 and the second fastening portion 71 to be disengaged from each other.

Given the above, in the joint angle adjustment mechanism, when the positioning member is operated to be disengaged from one of the toothed recesses, the adjustment mechanism can swing relative to the base to adjust the restriction angle of the two connecting members swinging relative to each other, and when the adjustment mechanism swings to the angle the user wants, by stopping driving the positioning member, then the positioning member can be engaged with one of the toothed recesses to enhance user safety.

In addition, when the lock member is in the first position, the restricting protrusion restricts one of the tooth portions, and the user can choose to make the restricting protrusion to restrict one of the tooth portions to adjust the angle of the two connecting members when locked.

Moreover, through the two second hook portions hooking the two first hook portions and the supporting portion abutting against the stepped portion, the elastic member can stably fixed on the slidable seat to nomially abut the slidable block toward a direction away from the center.

While we have shown and described various embodiments in accordance with the present invention, it should be clear to those skilled in the art that further embodiments may be made without departing from the scope of the present invention.

What is claimed is:

1. A joint angle adjustment mechanism, including:
a base, having a center and two side boards opposite to each other, the center defining an axial direction, at least one of the two side boards having a plurality of toothed recesses relative to the center, the plurality of toothed recesses being arranged curvedly, an opening of each said toothed recess facing the center;
two connecting members, respectively connected to the base, at least one of the two connecting members pivoted to the base;
a positioning mechanism, including at least one adjustment mechanism, each said adjustment mechanism axially pivoted to the base about the center, each said adjustment mechanism including a positioning assembly, the positioning assembly including a slidable seat, a positioning member and an elastic member, the positioning member being slidably arranged within the slidable seat and optionally moving radially to be engaged with or disengaged from one of the plurality of toothed recesses, the elastic member being arranged within the slidable seat, two ends of the elastic member curling and bending relatively inward around an axis parallel to a circumferential direction of the base so that the elastic member has an e-shaped cross-section, the elastic member abutting against the positioning member so that the positioning member has a tendency to be radially engaged with one of the plurality of toothed recesses; wherein the slidable seat has a receiving space therein, a side of the slidable seat along the axial direction has an opening which communicates with the receiving space, the positioning member includes a slidable block and a pin member, the slidable block is slidably arranged within the receiving space, the pin member is inserted between the slidable seat and the slidable block, and the pin member is normally engaged with one of the plurality of toothed recesses due to the elastic member;
wherein the slidable seat has at least one first hook portion in the receiving space, one of the two ends of the elastic member along a circumferential direction thereof forms at least one second hook portion, the at least one first hook portion and the at least one second hook portion hook with each other, and the other of the two ends of the elastic member opposite to the at least one second hook portion abuts against the slidable block.

2. The joint angle adjustment mechanism of claim 1, wherein each said adjustment mechanism further has a movable seat which is pivoted to the base, each said movable seat is saddled on the base, each said positioning assembly is arranged in one of the movable seats, one of two ends of the slidable block is disposed through and protrudes beyond the movable seat and the slidable seat, and the slidable block is operable from outside to drive the pin member to move radially to be engaged with or disengaged from one of the plurality of toothed recesses.

3. The joint angle adjustment mechanism of claim 2, wherein each of the side boards has a first pivotal groove at a face thereof opposite to the other one of the side boards, the adjustment mechanism has two said movable seats, each of the movable seats has two arm portions, and each of the two arm portions of one of the two movable seats is pivoted to one said first pivotal groove.

4. The joint angle adjustment mechanism of claim 3, wherein each of the two arm portions of one of the movable seats pivotally connected to one said first pivotal groove further has a second pivotal groove, each of the two arm portions of the other one of the two movable seats is pivotally connected to one said second pivotal groove, and a pivot shaft is disposed through the two side boards and the two arm portions of the two movable seats.

5. The joint angle adjustment mechanism of claim 1, wherein one of the two connecting members is fixed on the base, the other of the two connecting members is pivoted to the base, the joint angle adjustment mechanism further includes a lock member, the lock member is arranged on the base and movable to be in a first position and a second position, when the lock member is in the first position, the lock member unrestricts the one connecting member which is pivoted to the base, and when the lock member is in the second position, the lock member restricts the connecting member which is pivoted to the base so that the connecting member is unswingable relative to the base.

6. The joint angle adjustment mechanism of claim 5, wherein each of the side boards has a sliding slot at a face thereof facing the other one of the side boards, each of the sliding slots extends radially, the lock member is slidably arranged in the sliding slot, the sliding slot has a first fastening portion, the lock member has two second fastening portions, and when the lock member is in the first and second positions, the first fastening portion is correspondingly engaged with one of the two second fastening portions to prevent the lock member from sliding randomly.

7. The joint angle adjustment mechanism of claim 5, wherein one of the connecting members which is pivoted to the base has a plurality of tooth portions radially thereon, the lock member has a restricting protrusion radially thereon, and when the lock member is in the first position, the restricting protrusion restricts one of the plurality of tooth portions.

8. The joint angle adjustment mechanism of claim 1, wherein one of the two ends of the elastic member forms a forked section which has two leg portions, the two leg portions curl and bend and have one of the at least one second hook portions, an outer side of each of the two leg portions toward outside further has a supporting portion protruding therefrom, and each supporting portion abuts against a stepped portion in the receiving space.

9. The joint angle adjustment mechanism of claim 1, wherein each of the side boards further has a curved annular groove at a side thereof facing the other one of the side boards, each of the curved annular grooves communicates with the plurality of toothed recesses, and each said slidable seat is slidably arranged between the two curved annular grooves.

* * * * *